United States Patent [19]

Lampropoulos et al.

[11] Patent Number: 5,483,999
[45] Date of Patent: Jan. 16, 1996

[54] WASTE COLLECTION SYSTEM FOR CONTAINMENT AND DISPOSAL OF CONTAMINATED FLUIDS

[75] Inventors: Fred P. Lampropoulos, Salt Lake City; Richard L. Young, Alpine; Cidny A. Bushman, Midvale; Bryan R. Lampropoulos, Salt Lake City, all of Utah

[73] Assignee: Merit Medical Systems, Inc., Salt Lake City, Utah

[21] Appl. No.: 33,303

[22] Filed: Mar. 15, 1993

[51] Int. Cl.⁶ .................................................. F23G 5/12
[52] U.S. Cl. ................. 141/86; 141/311 A; 141/98; 141/110; 206/366; 604/110; 604/192
[58] Field of Search ................. 141/86, 88, 311 A, 141/98, 110; 137/312; 206/366, 370; 604/110, 192

[56] References Cited

U.S. PATENT DOCUMENTS

| | | | |
|---|---|---|---|
| Des. 330,417 | 10/1892 | Bell | D24/117 |
| 3,215,299 | 11/1965 | Coanda et al. | |
| 3,387,732 | 6/1968 | Jellies | |
| 3,537,498 | 11/1970 | Amand | |
| 3,581,928 | 6/1971 | Amand | 215/100 A |
| 3,635,367 | 1/1972 | Morita et al. | 215/100 A |
| 3,901,399 | 8/1975 | McPhee | 215/100 A |
| 4,088,166 | 5/1978 | Miller | |
| 4,090,541 | 5/1978 | Cammarata, III et al. | |
| 4,199,062 | 4/1980 | Johnston et al. | 206/525 |
| 4,232,721 | 11/1980 | Martin et al. | |
| 4,301,935 | 11/1981 | Gokcen et al. | 215/100 A |
| 4,308,904 | 1/1982 | Martin et al. | |
| 4,465,487 | 8/1984 | Nakamura et al. | 604/408 |
| 4,488,643 | 12/1984 | Pepper | 206/366 |
| 4,581,763 | 4/1986 | Olsen | 383/49 |
| 4,615,045 | 9/1986 | Siegel | 383/5 |
| 4,641,680 | 2/1987 | Been | 137/312 |
| 4,672,688 | 6/1987 | Kalkipsakis | 383/58 |
| 4,728,504 | 3/1988 | Nichols | 206/366 X |
| 4,845,487 | 7/1989 | Frantz et al. | |
| 4,850,807 | 7/1989 | Frantz et al. | 417/63 |
| 4,874,103 | 10/1989 | Quisenberry et al. | 206/366 X |
| 4,940,157 | 7/1990 | Inagaki | 206/366 X |
| 4,946,290 | 8/1990 | Matyja | 383/10 |
| 4,953,708 | 9/1990 | Beer et al. | 206/632 |
| 4,991,731 | 2/1991 | Osip | 215/232 |
| 5,023,119 | 6/1991 | Yamakoshi | 428/35.2 |
| 5,039,004 | 8/1991 | Simpson | 206/366 X |

(List continued on next page.)

FOREIGN PATENT DOCUMENTS

2251423  7/1992  United Kingdom .................. 206/366

*Primary Examiner*—Ernest G. Cusick
*Attorney, Agent, or Firm*—Workman Nydegger Jensen

[57] ABSTRACT

A waste collection system for receiving contaminated fluids in a manner which helps to prevent splashing of fluids or spilling them while they are being collected, thereby increasing protection to personnel, and which also keeps the fluids safely contained until ready for permanent disposal. In one presently preferred embodiment, the waste collection system includes a receptacle in which an absorbent pad is placed. The top of the receptacle is then sealed with a lid in an essentially fluid-tight fit. The surface of the lid is concave and slopes inwardly to a point at which an opening is formed, and a circular foam disc is placed at the opening. The foam material is provided with slits so that fluid can be introduced to the interior of the receptacle by either injecting a device such as a syringe through the slits or by permitting fluid to directly contact the foam material of the disc, which provides absorption and wicking action so that fluids will readily pass through the disc. Drainage channels are also formed on the surface of the lid, which is concave, for draining fluids that contact the surface of the lid quickly into the receptacle. A stabilizing support base with a non-skid surface receives and frictionally holds the container, and after fluids are contained, the support base can then be used by placing it onto the top of the receptacle and over the lid in a friction-tight seal so as to completely enclose the contaminated fluids within the receptacle, ready for permanent disposal.

113 Claims, 7 Drawing Sheets

U.S. PATENT DOCUMENTS

| | | | |
|---|---|---|---|
| 5,083,678 | 1/1992 | Waring | 222/92 |
| 5,100,000 | 3/1992 | Huseman | 206/554 |
| 5,116,139 | 5/1992 | Young et al. | 383/49 |
| 5,152,394 | 10/1992 | Hughes | 206/366 |
| 5,163,375 | 11/1992 | Withers et al. | 206/366 X |
| 5,167,193 | 12/1992 | Withers et al. | 206/366 X |
| 5,172,808 | 12/1992 | Bruno | 206/366 |
| 5,259,501 | 11/1993 | Withers et al. | 206/366 |
| 5,265,724 | 11/1993 | Dondlinger | 206/366 |

WASTE COLLECTION SYSTEM FOR CONTAINMENT AND DISPOSAL OF CONTAMINATED FLUIDS

BACKGROUND

1. Field of the Invention

The present invention relates to waste collection systems for containment and disposal of contaminated fluids. More particularly, the present invention relates to a waste collection system for receiving contaminated physiological fluids in a manner which helps to prevent splashing the fluids or spilling them, thereby increasing the protection to medical personnel, and which keeps the fluids safely contained until ready for permanent disposal.

2. The Prior State of the Art

Collection, containment, and safe disposal of contaminated fluids is increasingly becoming a concern for reasons of environmental protection as well as protection and safety of persons who must be involved in connection with the handling, collection and disposal of such fluids in the context of many different types of applications. Perhaps nowhere are the concerns greater with respect to protection of the environment and personnel than in the context of the handling and safe disposal of contaminated physiological fluids. A typical example where such physiological fluids must be safely handled and safely collected, contained, and then disposed of occurs on a daily basis in connection with procedures that are performed in the catheter lab of a hospital.

It is common practice in connection with many catheter lab procedures to have a table set up in the back of the catheter lab which is often referred to as the "back table." This table is used for setting up many types of medical instruments and their associated couplings to intravenous tubing and the like. The back table is also commonly used for collection and disposal of contaminated physiological fluids, both during and after a particular procedure has been performed.

For example, during angiography and angioplasty procedures, a great deal of blood and other fluids which may have been administered intravenously are accumulated. Doctors and medical personnel need a convenient system for collecting these fluids and disposing of them in a safe manner. This is particularly true due to the growing risk to health care personnel who may come in contact with blood or other physiological fluids which may have become contaminated with the HIV (AIDS) virus, hepatitis, or other communicable diseases. Thus, the health care industry is constantly looking for ways of improving the working environment for such health care professionals so as to make that environment safer during such procedures by minimizing the possibility of contamination from coming in contact with such contaminated fluids.

Presently, in most catheter labs, products which are currently used for purposes of receiving and containing contaminated fluids include such items as vinyl film bags with tubing lines which require attachment of a manifold or syringe for the collection of blood and other fluids during angiography or angioplasty procedures. Many catheter labs simply use open basins to collect waste or may let the contaminated fluid waste collect on an absorbent towel.

The current procedures and methods for collecting such contaminated fluids and disposing of them are inadequate for several reasons. Use of vinyl film bags with attached tubing lines and with attached manifolds and syringes often involves overly complicated and time consuming set up and interconnection of various components, as well as unduly complicated and costly inventories for parts and the like. In the case where open basins or absorbent towels are used, such procedures do not provide adequate protection against splash, spillage, and the like, and thus do not provide adequate protection for health care professionals.

PRINCIPAL OBJECTS AND BRIEF SUMMARY OF THE INVENTION

The present invention seeks to resolve the above and other problems which have been experienced in the art. More particularly, it is an important object of the present invention to provide a waste collection system for receiving contaminated fluids in a manner which helps to prevent splashing of fluids or spilling them while they are being collected, thereby increasing the protection to personnel, and which also keeps the fluids safely contained until ready for permanent disposal.

Another object is to increase the stability of a waste collection system so as to minimize the chance of tipping the waste collection system over and thus spilling the contents.

Still a further object is to keep contaminated fluids safely contained in a waste collection system after they have been collected until the waste collection system is ready for permanent disposal.

Still a further important object of the invention is to collect contaminated fluids in a manner so as to reduce the likelihood of splashing the fluids while they are being collected so as to provide effective containment of the fluids.

Briefly summarized, the above and other objects and advantages of the present invention are realized in a waste collection system which in one presently preferred embodiment is comprised of a receptacle in the shape of a molded plastic box that has four sidewalls and a bottom, and an open top. A snap ring is formed as a rim around the open top's periphery. An absorbent pad is placed in the box and the open top is then sealed by a molded plastic lid which has a shoulder around the periphery of the lid that is adapted to fit in a friction-type fit onto the snap ring around the periphery of the open top of the box. In this manner, the lid forms an essentially fluid-tight seal with the top ok the box, with the absorbent pad disposed inside the box.

The surface of the lid is concave and slopes inwardly to a point at which an opening is formed, and a circular disc constructed of a foam material is placed in the opening. The foam material of the circular disc provides absorption and wicking action for fluids contacting the foam materials so that the fluids will readily pass through the foam material without splashing and without beading up. The circular disc is also provided with a number of slits so that fluid can readily be injected, for example, by means of a syringe by sticking the end of the syringe through the slits formed in the disc and squirting the contents onto the absorbent pad contained within the box.

A series of drainage channels are also formed on the concave surface of the lid. Each channel extends underneath the circular, foam disc. The drainage channels provide for quick drainage of any contaminated fluids contacting the surface of the lid so as to drain them into the box and onto the absorbent pad contained therein.

In a further aspect of the invention, the waste collection system can also optionally include a combination member that serves as a stabilizing support base with a non-skid or skid resistant surface which receives and frictionally holds the box and helps to prevent it from slipping on the surface or tipping over. After the contaminated fluids are collected, the combination member can then be removed from the bottom of the box and placed onto the box and over the lid in a friction-tight seal so as to completely enclose the contaminated fluids within the box, ready for permanent disposal.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention in its presently understood best mode for making and using the same will be described with additional specificity and detail through the use of the accompanying drawings in which.

DETAILED DESCRIPTION OF THE PREFERRED EMBODIMENT

Additional objects and advantages of the invention will be set forth in the description which follows, or may be learned by the practice of the invention. The objects and advantages of the invention may be realized and obtained by means of the instruments and combinations particularly pointed out in the appended claims.

Figure 1:
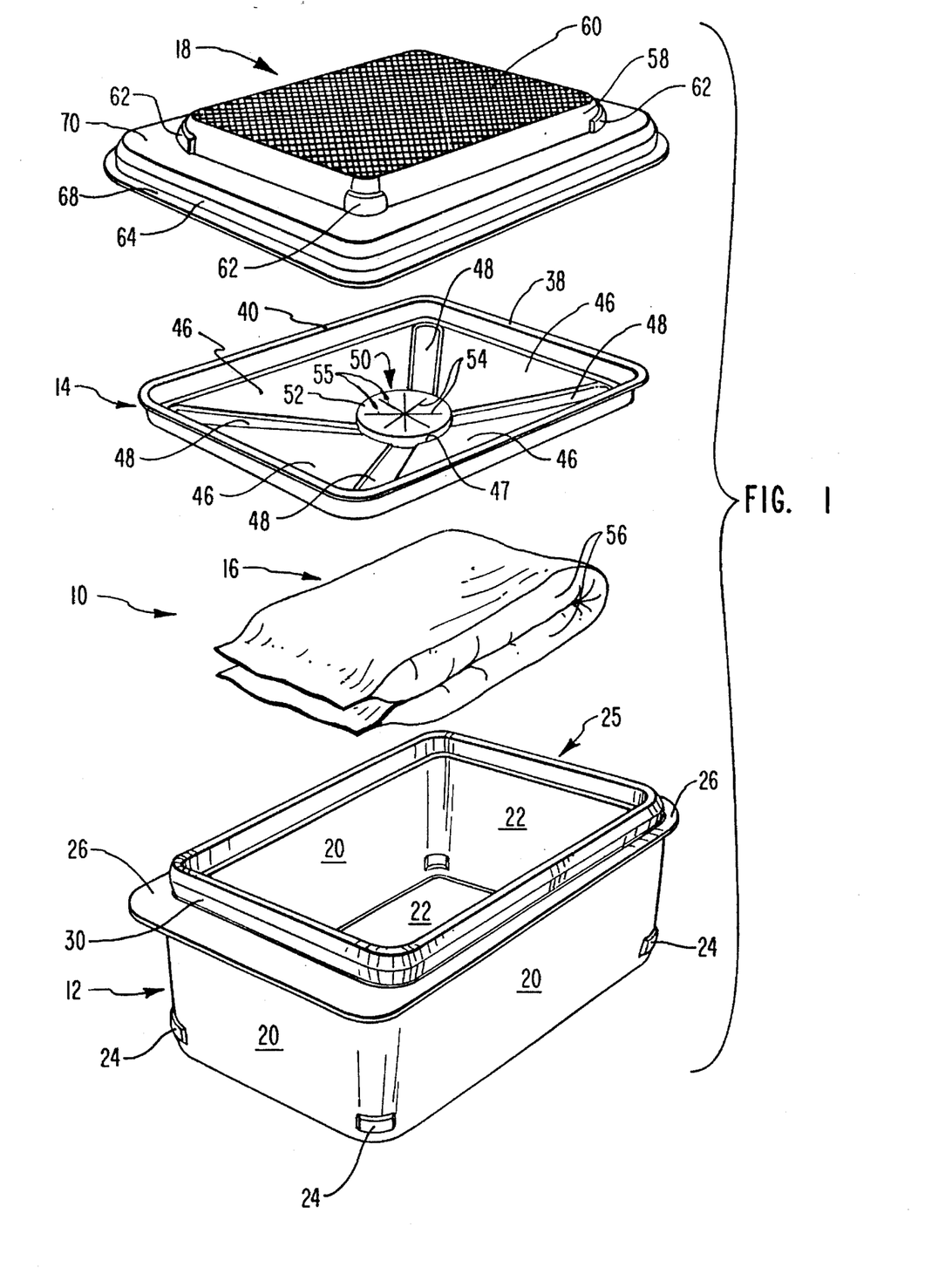
FIG. 1 is an exploded perspective view of one presently preferred embodiment of the waste collection system of the present invention.

Reference is first made to FIG. 1. The waste collection system of the present invention is generally designated at reference numeral 10. In one aspect of the present invention, the waste collection system 10 is comprised of a receptacle means for holding contaminated fluids introduced into the receptacle means. By way of illustration and example, the receptacle means may be provided by the receptacle generally designated at 12 which is comprised of a box having four sidewalls 20, a bottom 22 and an open top. The receptacle 12 may preferably be formed as a molded, unitary plastic member. The open top of the receptacle 12 or box is comprised of a snap ring which is generally designated at 25 and which is formed as a rim around the open top's periphery.

Figure 6:
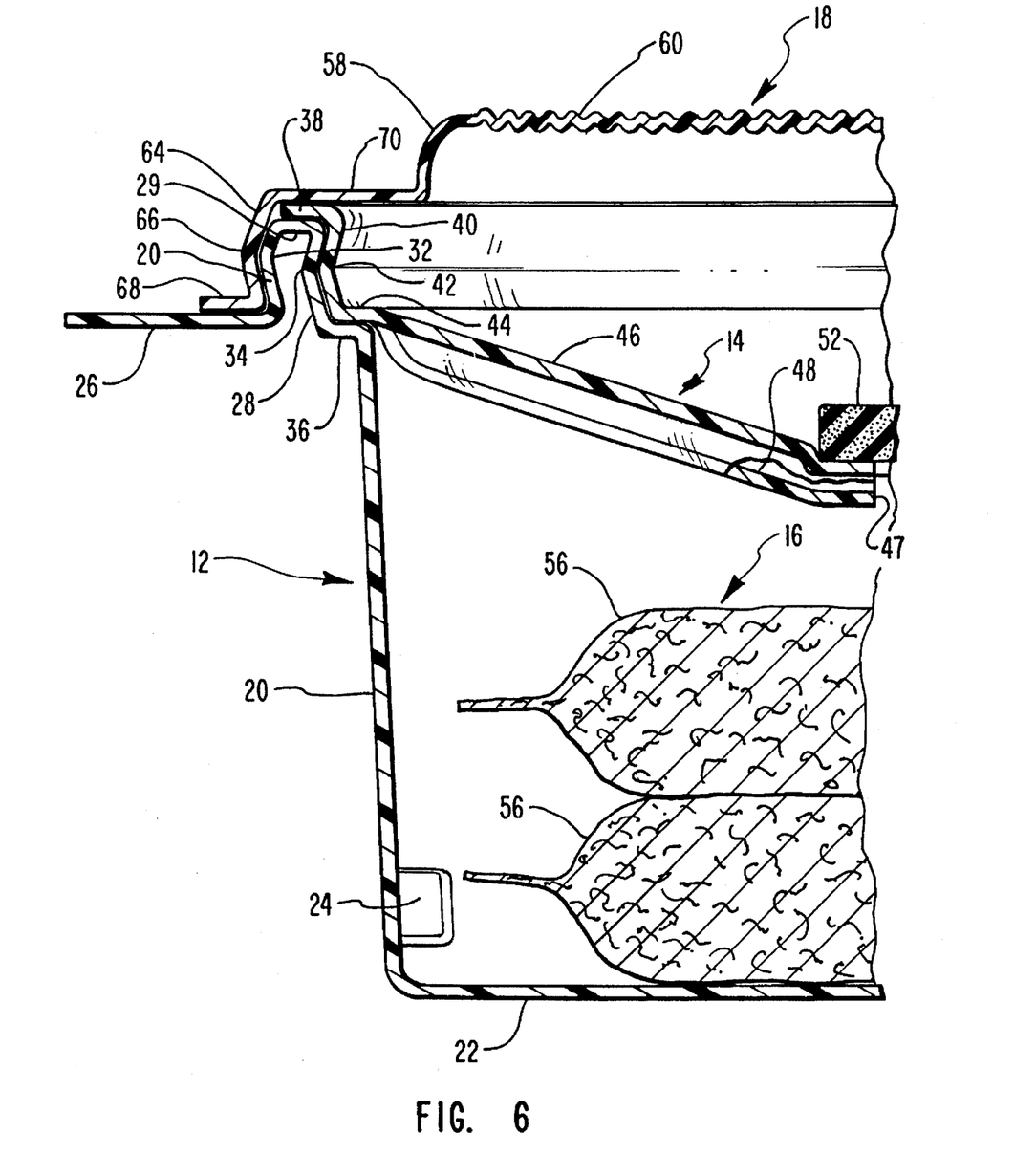
FIG. 6 is a cross-sectional view taken along line 6—6 of FIG. 5.

As shown best in the cross-sectional view of FIG. 6, the snap ring 25 (shown in FIG. 1) is molded as a continuous part of the sidewalls 20 in the presently preferred embodiment. Accordingly, the sidewalls 20 have a horizontal shoulder 36 formed at the top thereof. Shoulder 36 in turn is joined to an inner wall 28 that is bent at a point 34 so that the inner wall 28 is slightly concave. The inner wall 28 continues and is joined by a small horizontal member 29 to an outer wall 20. Outer wall 20 is also similarly bent at point 32 so that it is slightly convex. The outer wall 20 terminates at its lower end in a horizontal rim or shelf 26 which extends around the entire periphery of receptacle 12. As hereinafter more fully described, the inner wall 28 and outer wall 20 together form the snap ring 25 (shown in FIG. 1) which is used to provide sealing engagement with other parts of the waste collection system, both during collection of contaminated fluids, and for later sealing and closure of the contaminated fluids once the entire waste collection system is ready for permanent disposal.

With continued reference to both FIGS. 1 and 6, the receptacle 12 also includes in another aspect of the present invention stake means at each corner of the receptacle 12 for securing the receptacle at the corners. By way of illustration and example, and as more fully described hereinafter, the stake means is comprised of detents 24 which are adapted to frictionally engage corresponding pockets formed in a support base.

With continued reference to FIGS. 1 and 6 taken together, the waste collection system 10 is further comprised of containment means, joined to the receptacle 12 in an essentially fluid-tight manner for providing containment of the contaminated fluids within the receptacle 12. By way of illustration and example, the containment means of the presently preferred embodiment is shown as comprising a lid generally designated 14. The lid 14 is also preferably constructed as a unitary plastic member and molded as a single piece, and is also preferably transparent so that delivery of the fluids to the interior of receptacle 12 can be easily verified by visual inspection. The lid 14 is comprised of four downwardly sloping surfaces 46 which meet at an opening 47 which is formed at essentially the center of the lid 14.

In still a further aspect of the present invention, the waste collection system is further comprised of valve means, disposed on either the receptacle 12 or the lid 14, for permitting passage of contaminated fluids into the receptacle 12 without permitting the contaminated fluid to splash outside of the receptacle 12 and lid 14 as the contaminated fluid is introduced into the receptacle 12. By way of illustration of the presently preferred embodiment, the valve means is comprised of a circular disc 52 which is placed at the opening 47 formed in the center of lid 14. The circular disc 52 is comprised of a foam member formed from foam material that provides absorption and wicking action for fluids contacting the foam material, such that fluids will readily pass through the foam material without splashing and without beading up. In the presently understood best mode of the invention, the foam material is a natural die-cut foam of a type which is specified as 100 ppi SIF "z", manufactured and sold by Aspen Sales, 5258 Pinemont Drive, Suite B-200, Murray, Utah, 84123.

Figure 2:
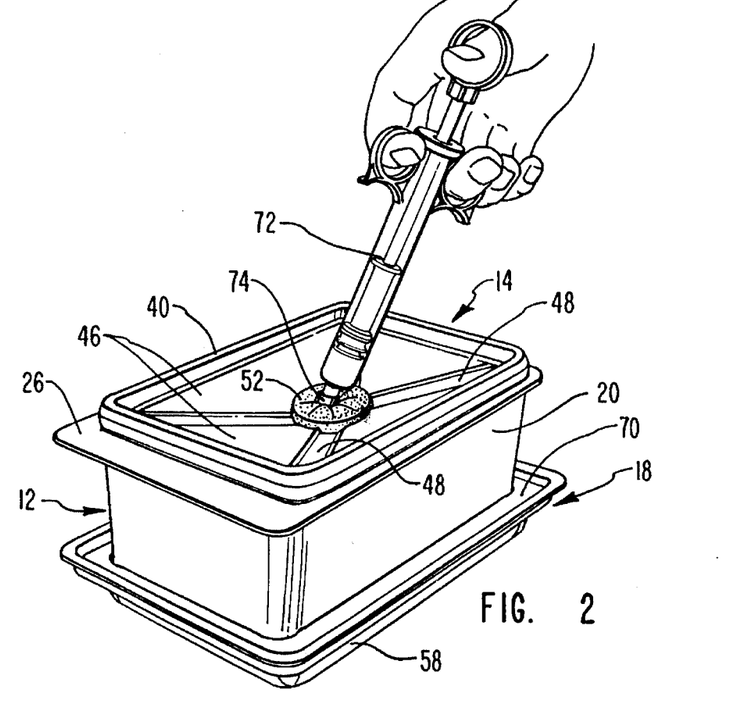
FIG. 2 is a perspective view which more particularly illustrates the combination member being used as a support base to securely hold the receptacle, and which also illustrates one presently preferred method for using the waste collection system for receiving contaminated fluids from a syringe.

As further illustrated, and particularly in FIGS. 1 and 2 taken together, the circular foam disc 52 is also provided with a plurality of slits 54 so as to form a plurality of flaps 55. The flaps 55, as best illustrated in FIG. 2, permit the entry of a device such as the tip 74 of a syringe 72 so as to provide entry through the circular foam member or disc 52 when injecting fluids into the interior of receptacle 12.

With further reference to FIGS. 1 and 6 taken together, in the presently preferred embodiment, the lid 14 is comprised of four sloping surfaces 46 which slope downwardly and terminate at the opening 47 at which the disc 52 is placed. Between each pair of sloped surfaces 46, there is a channel 48 that is formed. As shown best in FIG. 6, each channel 48 runs beneath the circular disc 52. Thus, channels 48 permit fluids which contact the surface of the lid 14 to be quickly channeled and drained into the interior of receptacle 12. Accordingly, channels 48 illustrate one presently preferred way of providing a drainage means for draining fluids dropped onto the lid into the interior of the receptacle 12. Thus, as illustrated for example in FIG. 3, fluids which are dropped directly onto the surface of the lid 14 can be quickly drained by means of the channels 48 to the interior of receptacle 12.

With reference to FIG. 6, the lid 14 is also comprised of a rim 44 which extends around the periphery of the lid 14 and which sits upon shoulder 36 of receptacle 12. The rim 44 is formed as a unitary part of a shoulder 40 which extends horizontally and which is bent at 42 so as to correspond with the bend 44 in the inner wall 28 of snap ring 25 on receptacle 12. Shoulder 40 terminates in an upper horizontal member 38 which sits in a corresponding fashion over the horizontal member 29 of snap ring 25. The dimensions of lid 14 relative to the open top of receptacle 12 are such that, as shown in FIG. 6, the shoulder 40 thus fits in a friction fit over the horizontal member 29 and inner wall 28 of snap ring 25 so as to provide a primary fluid-tight seal between the receptacle 12 and lid 14.

In still a further aspect of the present invention, the waste collection system can also further comprise a pad means disposed in the receptacle 12 for absorbing and holding contaminated fluid. By way of illustration and example, the pad means is shown as comprising an absorbent pad generally designated at 16 which is folded so as to form two layers 56. The upper layer sits directly beneath the circular foam disc 52 and the outlet to the channels 48 so that fluid which enters through the lid either by way of channels 48 or through circular foam disc 52 is readily absorbed and retained by the upper layer, whereas any fluid which reaches the bottom 22 of the receptacle 12 is readily absorbed and retained by the lower layer. The absorbent pad 16 may be comprised, for example, of a diaper-type pad which is doubled and which is comprised of a cotton top sheet with a wood pulp filler and a super absorbent polymer filler enclosed within the cotton top sheet. A suitable diaper-type absorbent pad of the type described may be obtained from Weyerhaeuser, located at 2469 East Fort Union Boulevard, Suite 100-2, Salt Lake City, Utah, 84121. The absorbent pad can also be optionally treated with a disinfectant such as a suitable disinfectant for killing the HIV (AIDS) virus, hepatitis, or other types of communicable viruses or bacteria.

Figure 3:
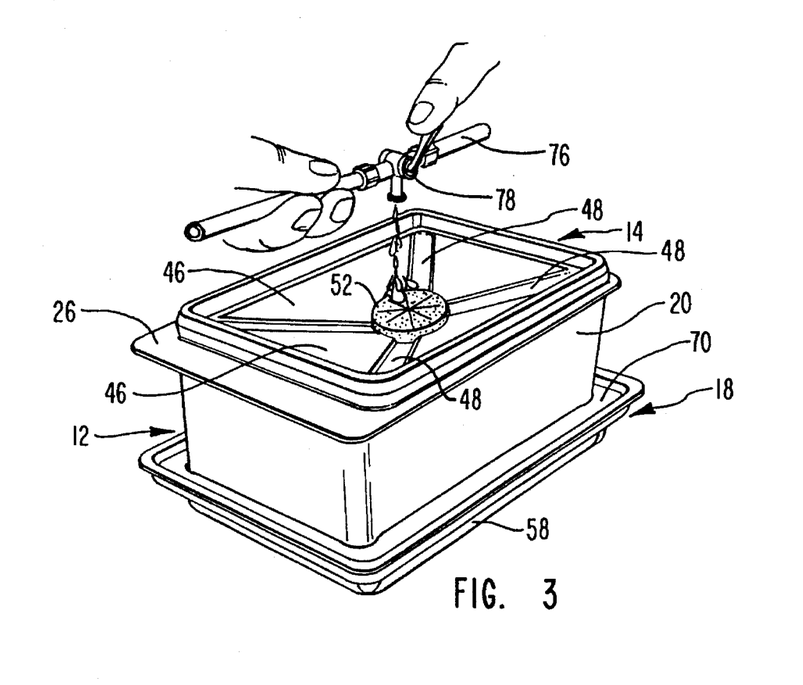
FIG. 3 is a perspective view similar to that of FIG. 2, which more particularly illustrates another preferred manner of using the waste collection system to collect contaminated fluids from an intravenous fluid line by expelling fluids from a stopcock in the line.
Figure 4:
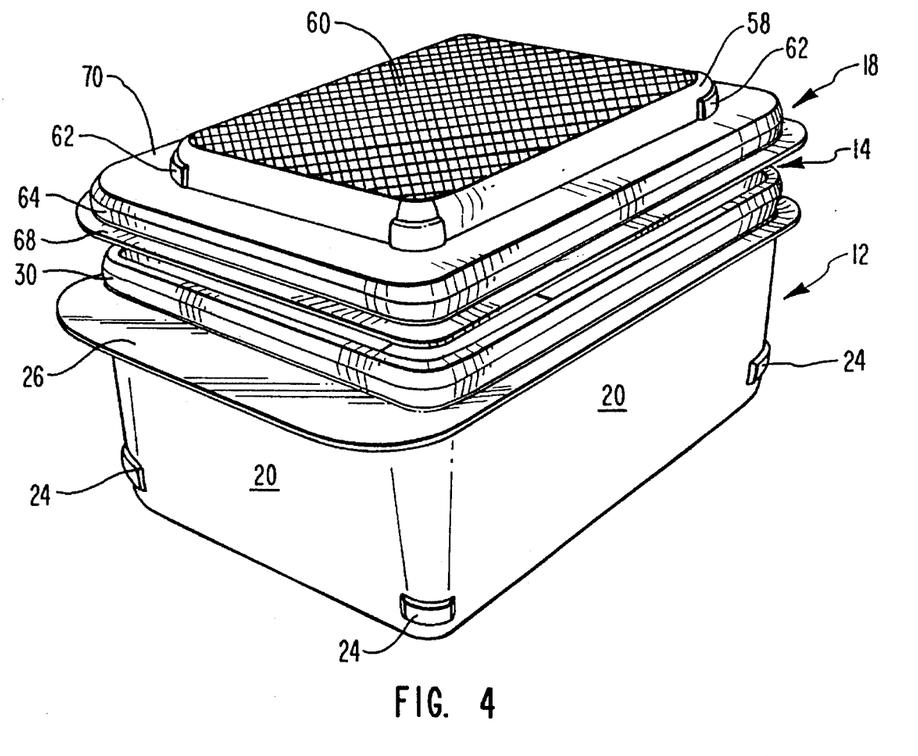
FIG. 4 is an exploded perspective view of the embodiment in FIG. 1, which more particularly illustrates removal of the combination member after the fluids have been collected and wherein the base member is now positioned ready for sealing the top of the container.

In still a further aspect of the present invention, the waste collection system 10 may be further comprised of a combination means for providing in combination both (1) support means for holding and stabilizing the receptacle 12 on a surface so as to help prevent the receptacle 12 from slipping on the surface or from spilling over while fluid is collected in the receptacle 12, and (2) enclosure means for placement onto the receptacle 12 and over the lid 14 so as to provide an essentially fluid-tight container ready for disposal after the fluid is collected. By way of illustration and example in the presently preferred embodiments, the combination means may be comprised of a base member generally designated at 18 which is formed as a unitary piece of molded plastic material. Base member 18 preferably includes a non-skid or skid resistant surface 60 which is formed at the bottom of a recess 58. Formed at the corners of recess 58 are pockets 62 which are designed to frictionally receive and hold the detents 24 which are formed at the four corners of the receptacle or box 12. Pockets 62 thus help to secure within the recess 58 the receptacle 12, and the non-skid surface 60 helps to keep the receptacle 12 from slipping or from being overturned. The base member 18 is shown in FIGS. 2 and 3, receiving the receptacle 12 in a friction-tight fit so as to provide non-skid, stabilizing support to receptacle 12 when the receptacle 12 is placed on a surface. In this configuration, while contaminated fluid is being collected in the receptacle 12, the base member 18 helps to prevent the receptacle 12 from being overturned or from slipping on a surface, thereby helping to stabilize the receptacle 12 while the fluids are collected.

Figure 5:
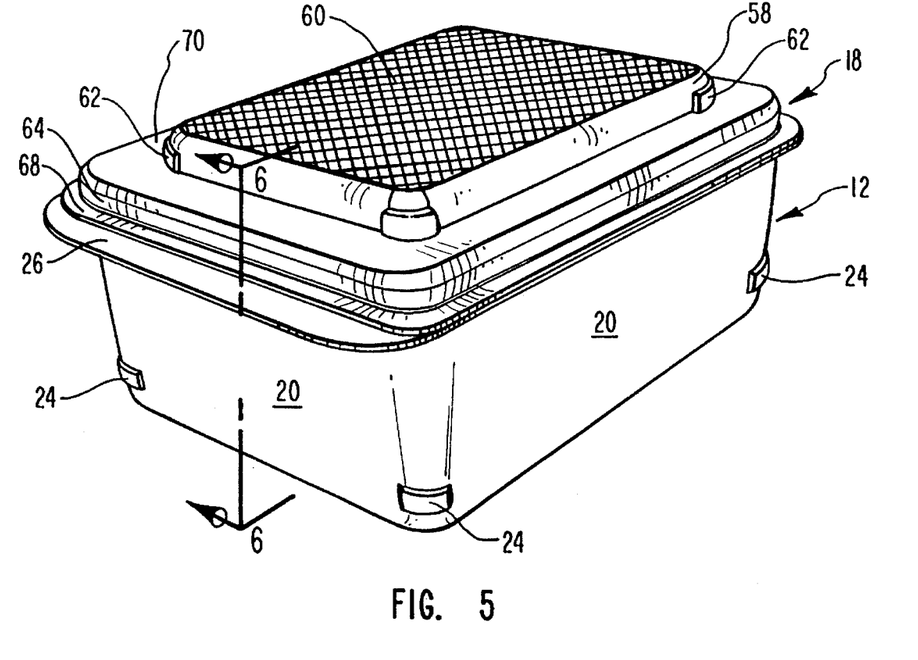
FIG. 5 is a perspective view of the waste collection system with the combination member sealed onto the top of the waste receptacle so that the entire waste collection system is now ready for permanent disposal.

FIGS. 1 and 4–6 taken together generally illustrate the manner in which the base member 14 can be placed onto the top of receptacle 12 after the fluids have been collected, so as to enclose the receptacle 12 in an essentially fluid-tight manner, ready for permanent disposal of the collected fluids. Thus, FIG. 4 generally illustrates the base member 18 removed from the bottom of receptacle 12 and ready for placement onto the top of receptacle 12, and FIG. 5 and 6 illustrate the base member as placed onto the top of receptacle 12 in an essentially fluid-tight fit.

With particular reference to FIG. 6, it will be seen that the base member 18 has a horizontal rim 70 that extends from recess 58 to shoulder 64. Shoulder 64 is bent at point 66 in a fashion which corresponds to the bend 32 in the outer wall 20 of snap ring 25 on receptacle 12. Shoulder 64 terminates in a small horizontal extension 68 that extends around the periphery of the base member 18. Accordingly, base member 18 is dimensioned so that shoulder 64 is designed to fit over the horizontal member 38 of lid 14 and over the outer wall 20 of snap ring 25 in a fluid-tight fit which is provided by means of the bent configuration provided by the outer wall 20 and the corresponding bent configuration of the shoulder 64. In this fashion, the shoulder 64 of the base member 18 provides an effective fluid-tight secondary seal between both the lid 14 and the receptacle 12. Thus, it will be appreciated that a double barrier against escape of contaminated fluids is provided by both the lid 14 and by the base member 18 once it is placed onto the top of receptacle 12 so as to assure that fluids are held within the receptacle 12 in an essentially fluid-tight manner once the fluids have been collected and are ready for permanent disposal. This increases protection against contamination during transport of the waste collection system 10 to an incinerator or other permanent disposal site.

Figure 7:
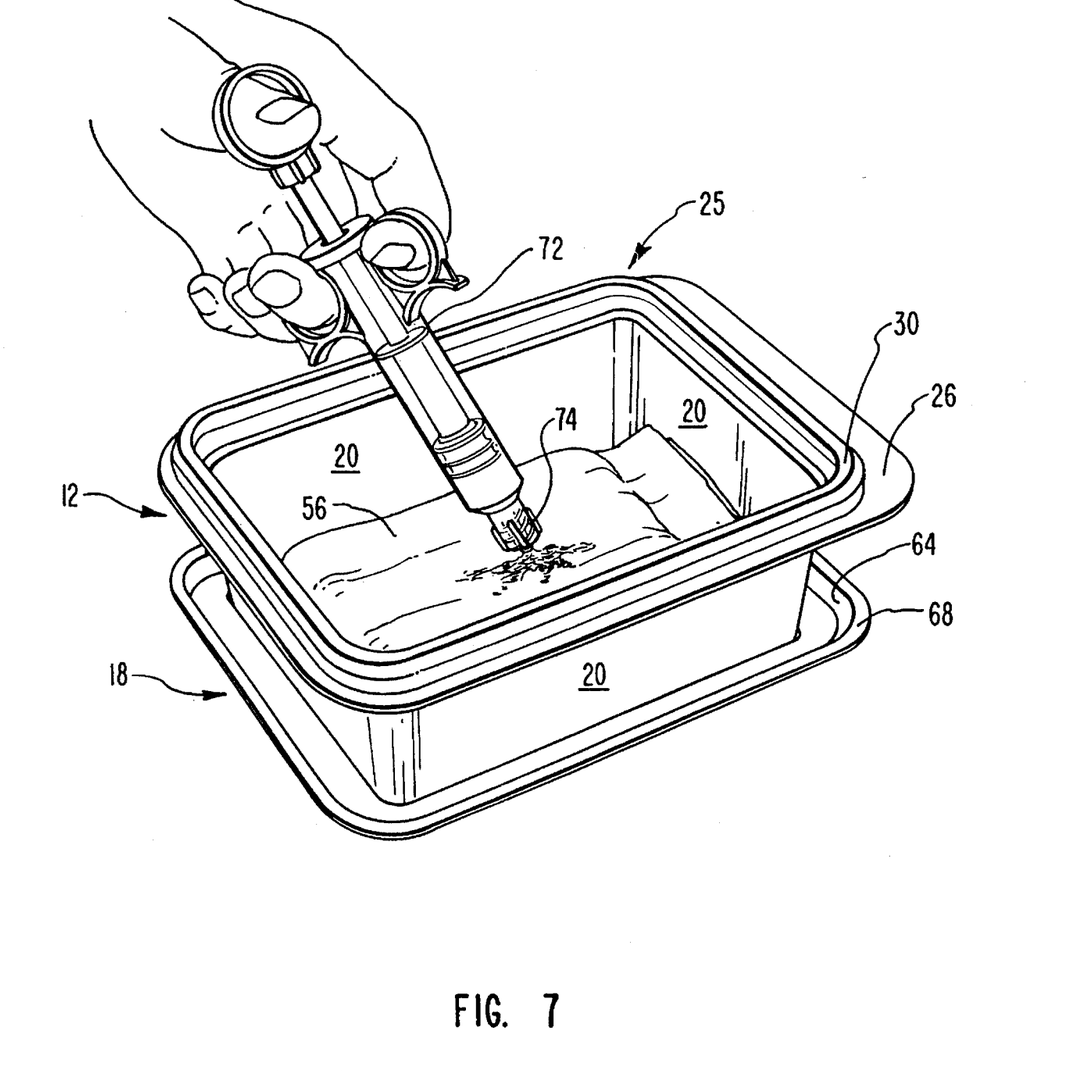
FIG. 7 is a perspective view of another embodiment of the present invention which particularly illustrates how the waste collection system may be utilized without the lid to receive contaminated fluids.

FIG. 7 generally illustrates another manner in which the waste collection system of the present invention can be used in an alternative way for collection and disposal of fluids. As illustrated in FIG. 7, the embodiment of the waste collection system shown in that illustration includes receptacle 12 and the base member 18 which also is used to enclose the top of the receptacle 12 after the fluid has been collected. In the embodiment of FIG. 7, the lid 14 has been eliminated so that fluids are expelled directly to the interior of the receptacle 12 and onto the absorbent pad 16 at the upper layer 56 thereof. After the fluids have been collected in receptacle 12, the base member 18 is then removed from the bottom of the receptacle 12 in the manner previously described, and is placed onto the snap ring 25 in a friction-tight fit so as to provide an essentially fluid-tight containment of the fluids collected in receptacle 12 and held by absorbent pad 16.

Figure 8:
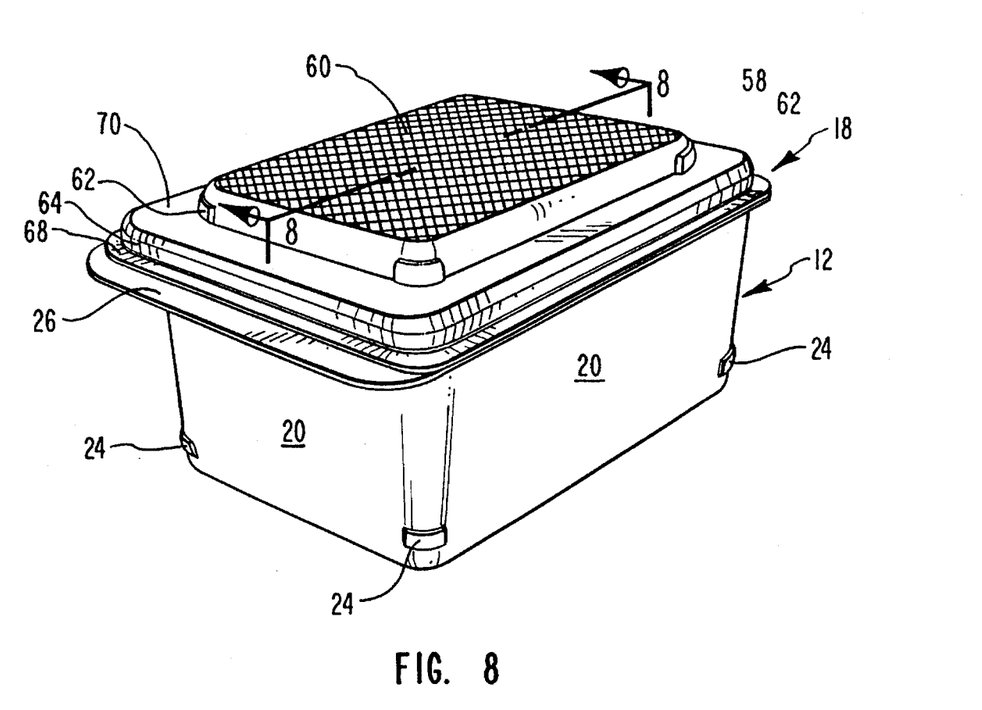
FIG. 8 is a perspective view of yet another embodiment of the invention wherein the waste collection system can be used without the lid and without the absorbent pad to receive and contain contaminated fluids.
Figure 9:
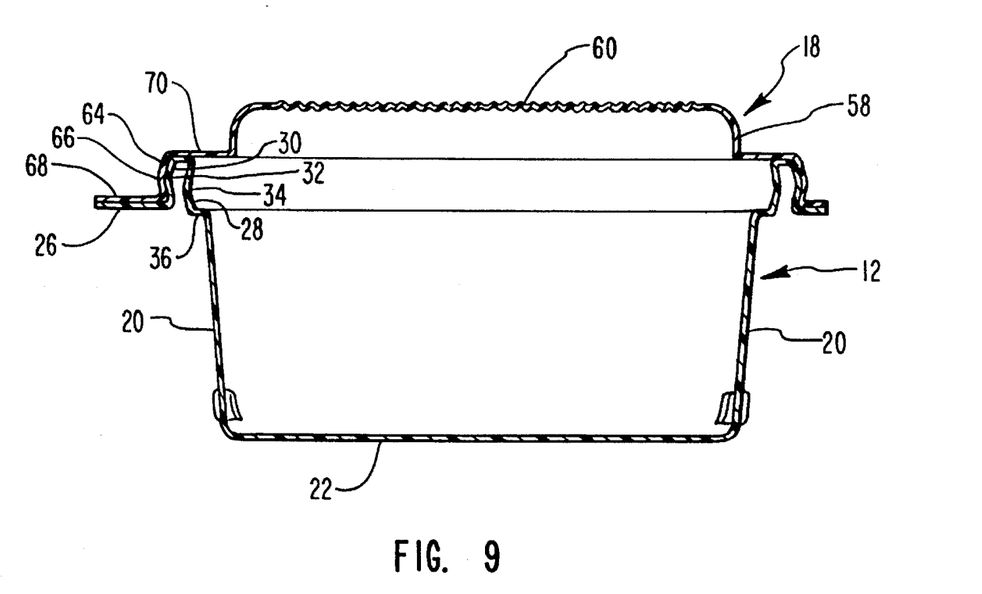
FIG. 9 is a cross-sectional view of the embodiment of FIG. 8.

FIGS. 8 and 9 illustrate still a further embodiment within the broadly defined inventive concepts of the waste collection system 10 of the present invention. In the embodiment as illustrated in FIGS. 8 and 9 taken together, the waste collection system utilizes only the receptacle 12 and the base member 18, without using either the lid 14 or the absorbent pad 16. Thus, in this embodiment, fluids are introduced directly into the interior of the receptacle 12 and afterwards the base member 18 is then placed onto the top of the receptacle 12 in the manner described previously so as to essentially seal the collected fluids in the receptacle 12 in a fluid-tight manner.

Figure 10:
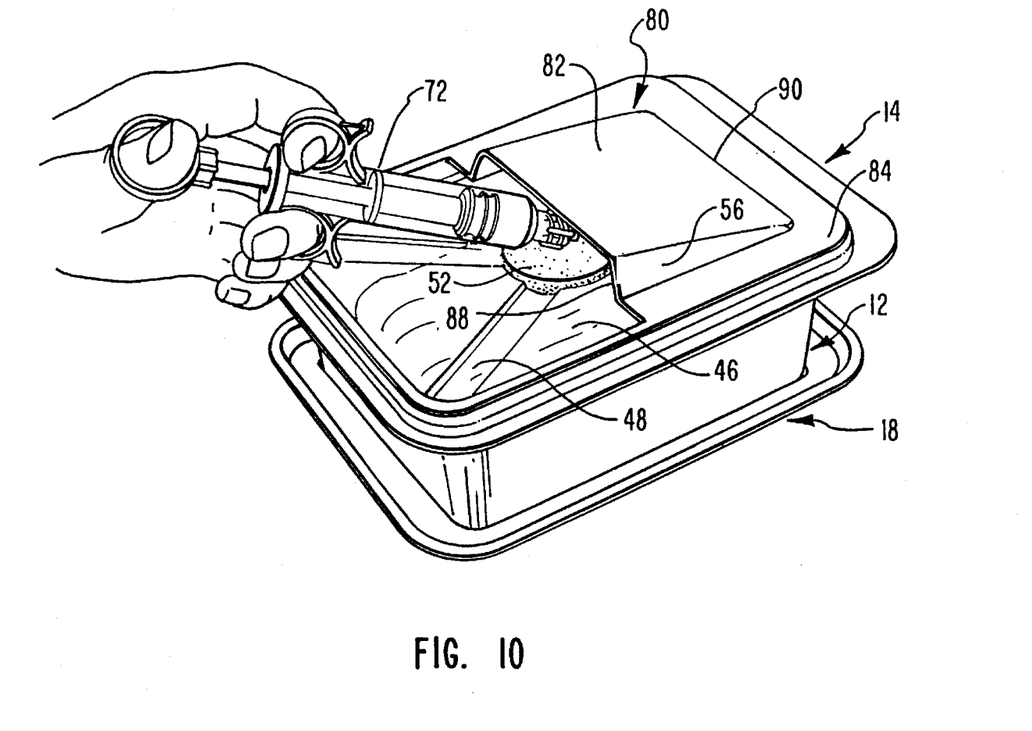
FIG. 10 is a perspective illustration of yet a further embodiment wherein the lid of the waste collection system is provided with a hood that prevents contaminated fluids from being splashed outside of the hood when being expelled.
Figure 11:
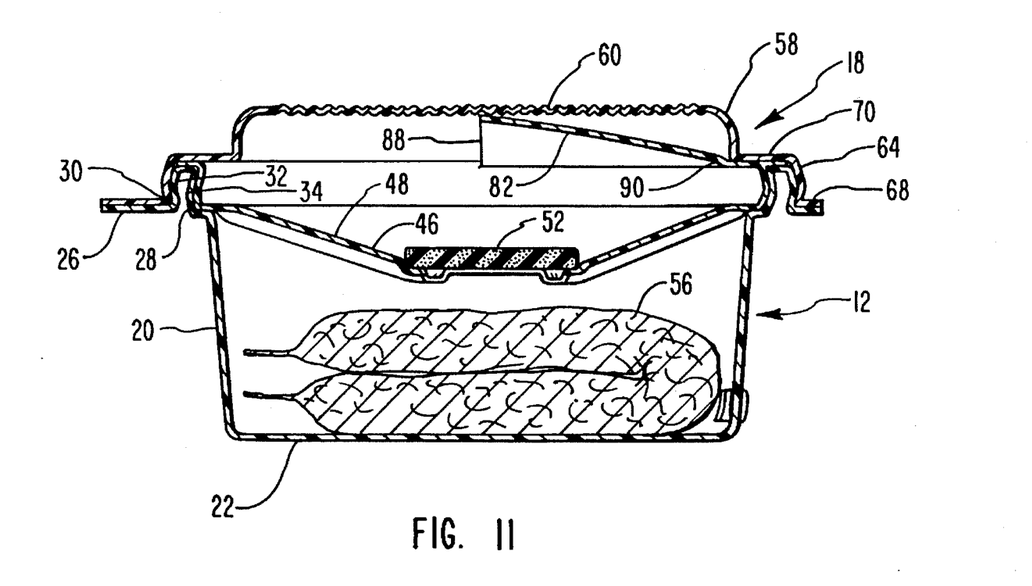
FIG. 11 is a cross-sectional view of the embodiment of FIG. 10 taken along lines 11—11 of FIG. 10.

In still a further embodiment of the present invention as shown in FIGS. 10 and 11 taken together, the lid 14 can also further comprise a hood means covering at least a portion of the lid for preventing contaminated fluids dropped or expelled onto the lid from splashing outside of the hood means. By way of illustration and example, the hood 82 is formed as an integral part of lid 14. Thus, as shown in FIGS. 10 and 11, lid 14 includes a horizontal surface 84 which meets the hood 82 at the downwardly tapering edge 90, with hood 82 being provided with tapered sides 56 which terminate in an opening 88. The hood 82 extends over approximately half of the lid 14 so that as illustrated in FIG. 10, a syringe 72 can be inserted into the opening 88 for purposes of injecting contaminated fluids onto the circular disc or pad 52. However, hood 82 prevents fluids from being splashed, thereby further helping to contain contaminated fluids so that they do not contact personnel.

As further illustrated in the cross-sectional view of FIG. 11, the hood 82 is designed so that the height of opening 88 is such that the entire hood 82 will fit within the recess 58 of base member 18 when the base member 18 is placed onto the top of receptacle 12 after the contaminated fluids have been collected and the receptacle 12 is sealed by the base member 18 for containment of the fluid prior to permanent disposal of the entire collection system. As will be appreciated, the hood means described above thus helps to provide further containment of contaminated fluids so as to prevent splashing or other escape of the contaminated fluids while they are being collected.

As will be appreciated from the foregoing, the waste collection system of the present invention provides for receiving contaminated fluids, such as physiological fluids or the like, in a manner which helps to prevent splashing of fluids or spilling them, thereby increasing the protection to personnel, while at the same time keeping the fluids safely contained until ready for permanent disposal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A waste collection system for receiving and containing contaminated fluids, comprising:

receptacle means for holding contaminated fluids introduced into the receptacle means;

containment means, joined to the receptacle means in an essentially fluid tight manner, for providing containment of the contaminated fluids within the receptacle means; and valve means formed of foam material, disposed on one of said receptacle means and said containment means, for permitting passage of contaminated fluids into the receptacle means without permitting the contaminated fluid to splash outside of the containment means and receptacle means as the contaminated fluid is introduced into the receptacle means.

2. A waste collection system as defined in claim 1 wherein said receptacle means comprises a box having four sidewalls and a bottom, and an open top.

3. A waste collection system as defined in claim 2 wherein the open top is comprised of a snap ring formed as a rim around the open top's periphery.

4. A waste collection system as defined in claim 3 wherein the box is molded as a unitary plastic member.

5. A waste collection system as defined in claim 2 wherein the box comprises stake means at each corner of the box for securing the box at the corners.

6. A waste collection system as defined in claim 1 wherein the containment means comprises a lid.

7. A waste collection system as defined in claim 6 wherein the valve means is disposed on said lid.

8. A waste collection system as defined in claim 7 wherein the foam material provides absorption and wicking action for fluids contacting the foam material such that fluids will readily pass through the foam material without splashing and without beading up.

9. A waste collection system as defined in claim 8 wherein the foam member comprises a plurality of flaps which provide entry through the foam member to the receptacle means.

10. A waste collection system as defined in claim 9 wherein the foam member comprises a circular disk located at essentially the lid's center.

11. A waste collection system as defined in claims 8 or 10 wherein the lid comprises drainage means for draining fluids dropped onto the lid into the receptacle means.

12. A waste collection system as defined in claim 11 wherein the drainage means comprises at least one sloped surface that slopes downwardly to meet the foam member disposed on the lid.

13. A waste collection system as defined in claim 11 wherein the drainage means comprises four surfaces sloping downwardly to meet the foam member disposed at the lid's center.

14. A waste collection system as defined in claim 13 wherein the drainage means further comprises a channel formed in the lid at the junction between each pair of sloped surfaces, and wherein each channel slopes downwardly to meet the foam member, and runs under the foam member so as to pass fluids collected in each channel under the foam member to the receptacle means.

15. A waste collection system as defined in claim 14 wherein the lid is molded as a unitary plastic member that is transparent.

16. A waste collection system as defined in claims 6 or 7 wherein the lid is molded as a unitary plastic member that is transparent.

17. A waste collection system as defined in claims 7 or 10 wherein said lid further comprises a hood means covering at least a portion of the lid for preventing contaminated fluids dropped or expelled onto the lid from splashing outside of the hood means.

18. A waste collection system as defined in claim 3 wherein the containment means comprises a lid.

19. A waste collection system as defined in claim 18 wherein the valve means is disposed on said lid.

20. A waste collection system as defined in claim 19 wherein the foam material provides absorption and wicking action for fluids contacting the foam material such that fluids will readily pass through the foam material without splashing and without beading up.

21. A waste collection system as defined in claim 20 wherein the foam member comprises a plurality of flaps which provide entry through the foam member to the receptacle means.

22. A waste collection system as defined in claim 21 wherein the foam member comprises a circular disk located at essentially the lid's center.

23. A waste collection system as defined in claims 20 or 22 wherein the lid comprises drainage means for draining fluids dropped onto the lid into the receptacle means.

24. A waste collection system as defined in claim 23 wherein the drainage means comprises at least one sloped surface that slopes downwardly to meet the foam member disposed on the lid.

25. A waste collection system as defined in claim 23 wherein the drainage means comprises four surfaces sloping downwardly to meet the foam member disposed at the lid's center.

26. A waste collection system as defined in claim 25 wherein the drainage means further comprises a channel formed in the lid at the junction between each pair of sloped surfaces, and wherein each channel slopes downwardly to meet the foam member, and runs under the foam member so as to pass fluids collected in each channel under the foam member to the receptacle means.

27. A waste collection system as defined in claim 26 wherein the lid is molded as a unitary plastic member that is transparent.

28. A waste collection system as defined in claims 18 or 19 wherein the lid is molded as a unitary plastic member that is transparent.

29. A waste collection system as defined in claims 19 or 22 wherein said lid further comprises a hood means covering at least a portion of the lid for preventing contaminated fluids dropped or expelled onto the lid from splashing outside of the hood means.

30. A waste collection system as defined in claim 18 wherein the lid comprises a shoulder formed around the lid's periphery, and wherein the shoulder fits onto the snap ring in a frictional fit so as to form an essentially fluid-tight primary seal between the lid and box.

31. A waste collection system as defined in claim 30 wherein the valve means is disposed on said lid.

32. A waste collection system as defined in claim 31 wherein the foam material provides absorption and wicking action for fluids contacting the foam material such that fluids will readily pass through the foam material without splashing and without beading up.

33. A waste collection system as defined in claim 32 wherein the foam member comprises a plurality of flaps which provide entry through the foam member to the receptacle means.

34. A waste collection system as defined in claim 33 wherein the foam member comprises a circular disk located at essentially the lid's center.

35. A waste collection system as defined in claim 34 wherein the lid comprises drainage means for draining fluids dropped onto the lid into the receptacle means.

36. A waste collection system as defined in claim 35 wherein the drainage means comprises four surfaces sloping downwardly to meet the foam member disposed at the lid's center.

37. A waste collection system as defined in claim 36 wherein the drainage means further comprises a channel formed in the lid at the junction between each pair of sloped surfaces, and wherein each channel slopes downwardly to meet the foam member, and runs under the foam member so as to pass fluids collected in each channel under the foam member to the receptacle means.

38. A waste collection system as defined in claim 37 wherein the lid is molded as a unitary plastic member that is transparent.

39. A waste collection system as defined in claim 1 further comprising pad means disposed in said receptacle means for absorbing and holding contaminated fluid.

40. A waste collection system as defined in claim 39 wherein the pad means is treated with a disinfectant.

41. A waste collection system as defined in claims 30 or 38 further comprising pad means disposed in the box for absorbing and holding contaminated fluid.

42. A waste collection system as defined in claim 41 wherein the pad means is treated with a disinfectant.

43. A waste collection system as defined in claim 1 further comprising support means for holding and stabilizing the receptacle means on a surface so as to help prevent the receptacle means from slipping on the surface or from spilling over.

44. A waste collection system as defined in claim 43 wherein said support means further comprises enclosure means for placement onto the receptacle means and over the containment means so as to provide an essentially fluid-tight container ready for disposal.

45. A waste collection system as defined in claim 5 further comprising support means for holding and stabilizing the receptacle means on a surface so as to help prevent the receptacle means from slipping on the surface or from spilling over.

46. A waste collection system as defined in claim 45 wherein the support means comprises a unitary plastic base member.

47. A waste collection system as defined in claim 46 wherein the base member comprises a recess shaped to receive in mating relationship the bottom and at least a portion of the four sidewalls of the box.

48. A waste collection system as defined in claim 47 wherein the recess comprises pocket means at each corner thereof for receiving in a friction fit the stake means at each corner of the box.

49. A waste collection system as defined in claim 48 wherein the recess comprises a non-skid surface means for contacting the surface.

50. A waste collection system as defined in claims 46 or 49 wherein the base member comprises enclosure means for placement of the base member onto the box and over the containment means so as to provide an essentially fluid-tight container ready for disposal.

51. A waste collection system as defined in claim 50 wherein the enclosure means comprises a shoulder formed around the periphery of the recess of the base member, and wherein the shoulder of the base member fits onto the snap ring and over the shoulder of the lid in a friction fit so as to form an essentially fluid-tight seal with the lid and the box.

52. A waste collection system as defined in claim 30 further comprising support means for holding and stabilizing the receptacle means on a surface so as to help prevent the receptacle from slipping on the surface or from spilling over.

53. A waste collection system as defined in claim 51 wherein the support means comprises a unitary plastic base member.

54. A waste collection system as defined in claim 52 wherein the base member comprises a recess shaped to receive in mating relationship the bottom and at least a portion of the four sidewalls of the box.

55. A waste collection system as defined in claim 53 wherein the recess comprises a non-skid surface means for contacting the surface.

56. A waste collection system as defined in claim 39 further comprising support means for holding and stabilizing the receptacle means on a surface so as to help prevent the receptacle means from slipping on the surface or from spilling over.

57. A waste collection system as defined in claim 56 wherein said support means further comprises enclosure means for placement onto the receptacle means and over the containment means so as to provide an essentially fluid-tight container ready for disposal.

58. A waste collection system for receiving and containing contaminated fluids, comprising:

receptacle means for holding contaminated fluids introduced into the receptacle means;

containment means, joined to the receptacle means in an essentially fluid tight manner, for providing containment of the contaminated fluids within the receptacle means;

valve means, disposed on one of said receptacle means and said containment means, for permitting passage of contaminated fluids into the receptacle means without permitting the contaminated fluid to splash outside of the containment means and receptacle means as the contaminated fluid is introduced into the receptacle means;

pad means disposed in said receptacle means for absorbing and holding contaminated fluid; and a single combination means for both (1) holding and stabilizing the receptacle means on a surface so as to help prevent the receptacle from slipping on the surface or from spilling over while fluid is collected in the receptacle means, and (2) for placement onto the receptacle means and over the containment means so as to provide an essentially fluid-tight container ready for disposal after the fluid is collected.

59. A waste collection system as defined in claim 58 wherein said receptacle means comprises a box having four sidewalls and a bottom, and an open top.

60. A waste collection system as defined in claim 59 wherein the open top is comprised of a snap ring formed as a rim around the open top's periphery.

61. A waste collection system as defined in claim 60 wherein the box is molded as a unitary plastic member.

62. A waste collection system as defined in claim 61 wherein the box comprises stake means at each corner of the box for securing the box at the corners.

63. A waste collection system as defined in claims 58 or 62 wherein the containment means comprises a lid.

64. A waste collection system as defined in claim 63 wherein the lid comprises a shoulder formed around the lid's periphery, and wherein the shoulder fits onto the snap ring in a frictional fit so as to form an essentially fluid-tight primary seal between the lid and box.

65. A waste collection system as defined in claim 63 wherein the valve means is disposed on said lid.

66. A waste collection system as defined in claim 65 wherein the valve means is comprised of a foam member formed from a foam material that provides absorption and wicking action for fluids contacting the foam material such that fluids will readily pass through the foam material without splashing and without beading up.

67. A waste collection system as defined in claim 66 wherein the foam member comprises a plurality of flaps which provide entry through the foam member to the receptacle means.

68. A waste collection system as defined in claim 67 wherein the foam member comprises a circular disk located at essentially the lid's center.

69. A waste collection system as defined in claim 68 wherein the lid comprises drainage means for draining fluids dropped onto the lid into the receptacle means.

70. A waste collection system as defined in claim 69 wherein the drainage means comprises four surfaces sloping downwardly to meet the foam member disposed at the lid's center.

71. A waste collection system as defined in claim 70 wherein the drainage means further comprises a channel formed in the lid at the junction between each pair of sloped surfaces, and wherein each channel slopes downwardly to meet the foam member, and runs under the foam member so as to pass fluids collected in each channel under the foam member to the receptacle means.

72. A waste collection system as defined in claim 71 wherein the lid is molded as a unitary plastic member that is transparent.

73. A waste collection system as defined in claim 72 wherein said lid further comprises a hood means covering at least a portion of the lid for preventing contaminated fluids dropped or expelled onto the lid from splashing outside of the hood means.

74. A waste collection system as defined in claim 73 wherein the pad means is treated with a disinfectant.

75. A waste collection system as defined in claim 74 wherein the support means comprises a unitary plastic base member.

76. A waste collection system as defined in claim 75 wherein the base member comprises a recess shaped to receive in mating relationship the bottom and at least a portion of the four sidewalls of the box.

77. A waste collection system as defined in claim 76 wherein the recess comprises pocket means at each corner thereof for receiving in a friction fit the stake means at each corner of the box.

78. A waste collection system as defined in claim 77 wherein the recess comprises a non-skid surface means for contacting the surface.

79. A waste collection system as defined in claim 78 wherein the enclosure means comprises a shoulder formed around the periphery of the recess of the base member, and wherein the shoulder of the base member fits onto the snap ring and over the shoulder of the lid in a friction fit so as to form an essentially fluid-tight secondary seal with the lid and the box.

80. A waste collection system as defined in claim 58 wherein the support means comprises a unitary plastic base member.

81. A waste collection system as defined in claim 80 wherein the base member comprises a recess shaped to receive in mating relationship the receptacle means bottom.

82. A waste collection system as defined in claim 81 wherein the recess comprises a non-skid surface means for contacting the surface.

83. A waste collection system as defined in claim 82 wherein the enclosure means comprises a shoulder formed around the periphery of the recess of the base member, and wherein the shoulder of the base member fits onto the receptacle means top in a friction fit so as to form an essentially fluid-tight seal with the receptacle means top.

84. A waste collection system for receiving and containing contaminated fluids comprising:

a unitary box comprising four sidewalls, a bottom, an open top, and a snap ring formed as a rim around the open top's periphery;

pad means disposed in the box for absorbing and retaining contaminated fluids introduced into the box;

lid means for enclosing the open top of the box, the lid means comprising a shoulder formed around the lid's periphery such that the shoulder fits onto the snap ring of the box in a frictional fit so as to form an essentially fluid-tight primary seal between the lid and the box, and the lid means further comprising an opening formed therein;

a foam member disposed at the opening formed in the lid and comprising a foam material that provides absorption and wicking action for fluids contacting the foam material such that fluids will readily pass through the foam material without splashing and without beading up, and further comprising a plurality of flaps which provide entry through the foam member to the box interior; and a combination means for providing in combination both (1) a bottom member for holding and stabilizing the box on a surface so as to help prevent the box from slipping on the surface or from spilling over while fluids are collected in the box, and (2) a top member for placement onto the box over the lid means so as to provide an enclosed, essentially fluid-tight container ready for disposal after the fluids are collected, and said combination means comprising a shoulder formed around the periphery of the top member so as to fit onto the snap ring and over the shoulder of the lid means in a friction fit so as to form an essentially fluid-tight secondary seal with the lid means and the box.

85. A waste collection system as defined in claim 84 wherein the box comprises stake means at each corner of the box for securing the box at the corners.

86. A waste collection system as defined in claim 85 wherein the box is molded as a unitary plastic member and wherein the combination means comprise a unitary plastic base member, and wherein the base member comprises a recess shaped to receive in mating relationship the bottom and at least a portion of the four sidewalls of the box.

87. A waste collection system as defined in claim 86 wherein the recess comprises pocket means at each corner thereof for receiving in a friction fit the stake means at each corner of the box.

88. A waste collection system as defined in claim 87 wherein the recess comprises a non-skid surface means for contacting the surface.

89. A waste collection system as defined in claim 88 wherein the lid means comprises drainage means for draining fluids dropped onto the lid into the receptacle means.

90. A waste collection system as defined in claim 89 wherein the drainage means comprises four surfaces sloping downwardly to meet the foam member disposed at the lid's opening.

91. A waste collection system as defined in claim 90 wherein the drainage means further comprises a channel formed in the lid means at the junction between each pair of sloped surfaces, and wherein each channel slopes downwardly to meet the foam member, and runs under the foam member so as to pass fluids collected in each channel under the foam member to the pad means disposed in the box.

92. A waste collection system as defined in claim 91 wherein the lid means is molded as a unitary plastic member that is transparent.

93. A waste collection system as defined in claim 91 wherein the pad means is treated with a disinfectant.

94. A waste collection system as defined in claim 93 wherein said lid means further comprises a hood means covering at least a portion of the lid means for preventing contaminated fluids dropped or expelled onto the lid from splashing outside of the hood means.

95. A waste collection system for receiving and containing contaminated fluids, comprising:

receptacle means for holding contaminated fluids introduced into the receptacle means;

containment means, joined to the receptacle means in an essentially fluid tight manner, for providing containment of the contaminated fluids within the receptacle means, and wherein the containment means comprises a lid;

valve means, disposed on one of said receptacle means and said containment means, for permitting passage of contaminated fluids into the receptacle means without permitting the contaminated fluid to splash outside of the containment means and receptacle means as the contaminated fluid is introduced into the receptacle means; and a single combination means for providing in combination both (1) support means for holding and stabilizing the receptacle means on a surface so as to help prevent the receptacle means from slipping on the surface or from spilling over while fluid is collected in the receptacle means, and (2) enclosure means for placement onto the receptacle means and over the containment means so as to provide an essentially fluid-tight container ready for disposal after the fluid is collected.

96. A waste collection system as defined in claim 95 wherein said receptacle means comprises a box having four sidewalls and a bottom, and an open top.

97. A waste collection system as defined in claim 96 wherein the open top is comprised of a snap ring formed as a rim around the open top's periphery.

98. A waste collection system as defined in claim 97 wherein the box comprises stake means at each corner of the box for securing the box at the corners.

99. A waste collection system as defined in claim 98 wherein the box is molded as a unitary plastic member and wherein the combination means comprise a unitary plastic base member, and wherein the base member comprises a recess shaped to receive in mating relationship the bottom and at least a portion of the four sidewalls of the box.

100. A waste collection system as defined in claim 99 wherein the recess comprises pocket means at each corner thereof for receiving in a friction fit the stake means at each corner of the box.

101. A waste collection system as defined in claim 100 wherein the recess comprises a non-skid surface means for contacting the surface.

102. A waste collection system as defined in claim 101 wherein the enclosure means comprises a shoulder formed around the periphery of the recess of the base member, and wherein the shoulder of the base member fits onto the snap ring in a friction fit so as to form an essentially fluid-tight seal with the lid and the box.

103. A waste collection system as defined in claims 95 or 102 further comprising pad means disposed in said receptacle means for absorbing and holding contaminated fluid.

104. A waste collection system as defined in claim 103 wherein the pad means is treated with a disinfectant.

105. A waste collection system as defined in claim 95 wherein the valve means is disposed on said lid.

106. A waste collection system as defined in claim 105 wherein the valve means is comprised of a foam member formed from a foam material that provides absorption and wicking action for fluids contacting the foam material such that fluids will readily pass through the foam material without splashing and without beading up.

107. A waste collection system as defined in claim 106 wherein the foam member comprises a plurality of flaps which provide entry through the foam member to the receptacle means.

108. A waste collection system as defined in claim 107 wherein the foam member comprises a circular disk located at essentially the lid's center.

109. A waste collection system as defined in claim 108 wherein the lid comprises drainage means for draining fluids dropped onto the lid into the receptacle means.

110. A waste collection system as defined in claim 109 wherein the drainage means comprises four surfaces sloping downwardly to meet the foam member disposed at the lid's center.

111. A waste collection system as defined in claim 110 wherein the drainage means further comprises a channel formed in the lid at the junction between each pair of sloped surfaces, and wherein each channel slopes downwardly to meet the foam member, and runs under the foam member so as to pass fluids collected in each channel under the foam member to the receptacle means.

112. A waste collection system as defined in claim 111 wherein the lid is molded as a unitary plastic member that is transparent.

113. A waste collection system as defined in claim 112 wherein said lid further comprises a hood means covering at least a portion of the lid for preventing contaminated fluids dropped or expelled onto the lid from splashing outside of the hood means.

* * * * *